(12) United States Patent
Snyder et al.

(10) Patent No.: US 7,785,352 B2
(45) Date of Patent: Aug. 31, 2010

(54) MODULAR SPINAL FIXATION SYSTEM

(75) Inventors: Brian D. Snyder, Westwood, MA (US);
Edward J. Vresilovic, Ardmore, PA (US); Hemal P. Mehta, Washington, DC (US); John A. Muller, Boston, MA (US)

(73) Assignee: Mass Modular Spine Group, Inc., Westwood, MA (US)

( * ) Notice: Subject to any disclaimer, the term of this patent is extended or adjusted under 35 U.S.C. 154(b) by 0 days.

(21) Appl. No.: 11/879,023

(22) Filed: Jul. 13, 2007

(65) Prior Publication Data
US 2008/0051789 A1 Feb. 28, 2008

Related U.S. Application Data

(60) Provisional application No. 60/807,238, filed on Jul. 13, 2006.

(51) Int. Cl.
*A61B 17/70* (2006.01)
(52) U.S. Cl. .................................. 606/263; 606/264
(58) Field of Classification Search .......... 606/263–279
See application file for complete search history.

(56) References Cited

U.S. PATENT DOCUMENTS

| | | | | |
|---|---|---|---|---|
| 4,805,602 A * | 2/1989 | Puno et al. | .................. | 606/267 |
| 5,176,680 A | 1/1993 | Vignaud et al. | | |
| 5,499,983 A * | 3/1996 | Hughes | ...................... | 606/267 |
| 5,545,166 A | 8/1996 | Howland | | |
| 6,077,262 A * | 6/2000 | Schlapfer et al. | ............ | 606/305 |
| 6,264,658 B1 * | 7/2001 | Lee et al. | ..................... | 606/254 |
| 6,325,802 B1 * | 12/2001 | Frigg | ......................... | 606/263 |
| 6,355,039 B1 * | 3/2002 | Troussel et al. | ............. | 606/264 |

* cited by examiner

*Primary Examiner*—Eduardo C Robert
*Assistant Examiner*—Mary Hoffman
(74) *Attorney, Agent, or Firm*—Wayne A. Keown; Preti Flaherty

(57) ABSTRACT

A spinal fixation system having a modular construction to allow universal application to varying spine anatomy and load requirements of individual vertebral attachment members, while reducing requirements for large inventories to optimize spinal fixation. Modularity allows the individual attachment members, once attached optimally to bone, to be attached to a variety of interconnecting structural members optimized for load carrying capacity.

15 Claims, 10 Drawing Sheets

MODULAR SPINAL FIXATION SYSTEM

BACKGROUND OF THE INVENTION

1. Field of the Invention

The invention relates to apparatus and methods for treating spinal disorders. More particularly, the invention relates to spinal fixation systems.

2. Summary of the Related Art

The human spine is a system of articulated vertebral segments with tissues including vertebrae, intervertebral discs, facet joints, ligaments, and muscles. The human spine generally includes 24 vertebrae and the sacrum. These 24 vertebrae are designated from the head to the pelvis (cervical, thoracic, lumbar, and sacral). There are 7 cervical vertebrae, 12 thoracic vertebrae, 5 lumbar vertebrae (although this number may vary from 4 to 6 lumbar vertebrae in some humans), and 4 sacral vertebrae. The spine generally includes 25 articulations; each bone articulates with the one above and below. The superior C1 vertebra articulates with the skull and the inferior L5 vertebra articulates with the sacrum. With two exceptions, articulations between the vertebrae are through intervertebral discs and bilateral facet joints. The exceptions are the occipital-C1 and C1-C2 articulations. In addition to the vertebral discs and facet joints, other structural elements of the vertebrae include ligaments which connect and allow constrained mobility of the vertebrae, and musculature attachments through tendons to fixation points on the vertebrae to allow motion and maintain stability. The spine functions mechanically to protect the neurological elements of the spinal cord, to bear load and maintain posture, and to allow motion of the trunk and neck. Failure of any structural components of the spine as a result of disease or injury may lead to loss of the mechanical integrity of the spine, which may lead to neurological injury, mechanical instability, and deformity.

Loss of mechanical integrity of the spine may result from congenital or developmental abnormality, metabolic disorder, tumor, infection, trauma, arthritis, and degenerative disc diseaseor injury to any of the functional units of the spine, including vertebrae, intervertebral discs, facet joints, ligaments, and muscles. Ultimately, this can lead to pain, loss of function, and/or neurological impairment.

One of the main treatment modalities for loss of mechanical integrity of the spine has been the use of spinal fixation systems. These systems function to restore the mechanical integrity of the spine, by improving spine stability and correcting deformity.

A typical spinal fixation system includes 2 primary components: bone anchors and structural members. Bone anchors allow mechanical connection to vertebrae and may include, but are not limited to, such fixation means as screws, hooks, wires, and clips. Structural members allow interconnection between the bone anchors and they include, but are not limited to, such objects as rods or plates. The strategies for correcting mechanical instability and spinal deformity are varied, but typically allow for multiple points of fixation to the spine above and below the unstable segments or areas of deformity. Structural members are attached to these multiple points of spine fixation to the spine, providing mechanical stability and/or correction of deformity by supporting load and transmitting corrective forces and moments.

There are a variety of spinal fixation systems; for example, U.S. Pat. No. 5,176,680 discloses a device for fixing a spinal rod to vertebral screws, in which a spinal rod is passed through a split ring which is positioned between the prongs of a vertebral screw having a forked head. This assembly is locked into place by a locking screw threaded between the prongs of the forked head and onto the split ring. Similarly, U.S. Pat. No. 5,545,166 discloses a spinal fixation system that includes a plurality of anchor screws, clamp assemblies, pivot blocks, clamp blocks and rods that are implanted along a patient's spine to fix two or more adjacent vertebrae relative to each other. The mechanical functional requirements are varied over the spine. This results in variable loading and anatomic variation within the spine. This variation in load and anatomy has resulted in a large variety of sizes and types of anchor fixations to the vertebrae, as well as variation in size and strength of the structural members. The great variability in size and load carrying capacity of various portions of the spine has resulted in spinal fixation systems specifically adapted to the major areas of spine, such as cervical, thoracic, and lumbar vertebrae in both children and adults. Due to the high variability in anatomy and effect of disease, current systems include a large number of attachment members with customized rod and/or plate connectors, each of which is a unitary structure adapted to a particular area and application within the spine. Attachment and structural members adapted to one area of the spine are not readily adaptable for use in other areas of the spine. As a consequence, a very large inventory of different spine systems with specialized attachment members and connectors are needed for universal spine instrumentation. Therefore, there is a need for a new spinal fixation system that overcomes the lack of adaptability and universality of current spine systems comprised of functionally unique components requiring large inventories of various components that are often rarely used. Ideally, a spinal instrumentation system that allows universal fixation of all regions of the spine in either children or adults for a myriad of pathologic conditions and loading requirements with a minimum number of unique structural elements would reduce inventories, production, and shipping expenses.

BRIEF SUMMARY OF THE INVENTION

The invention provides a new spinal fixation system that overcomes the limitations of the currently available systems. The system has a modular construction to allow universal application to a variety of vertebral anatomies and load requirements with a minimum number of functionally unique components. Modularity is achieved by allowing attachment members optimized for attachment to a particular vertebra to be attached to any sized connector used to secure a matching structural member. Modularity allows the optimal attachment members, once affixed to the vertebra, to be attached to a variety of structural members optimized to support load and/or correct deformity.

DETAILED DESCRIPTION OF THE PREFERRED EMBODIMENTS

Figure 1:
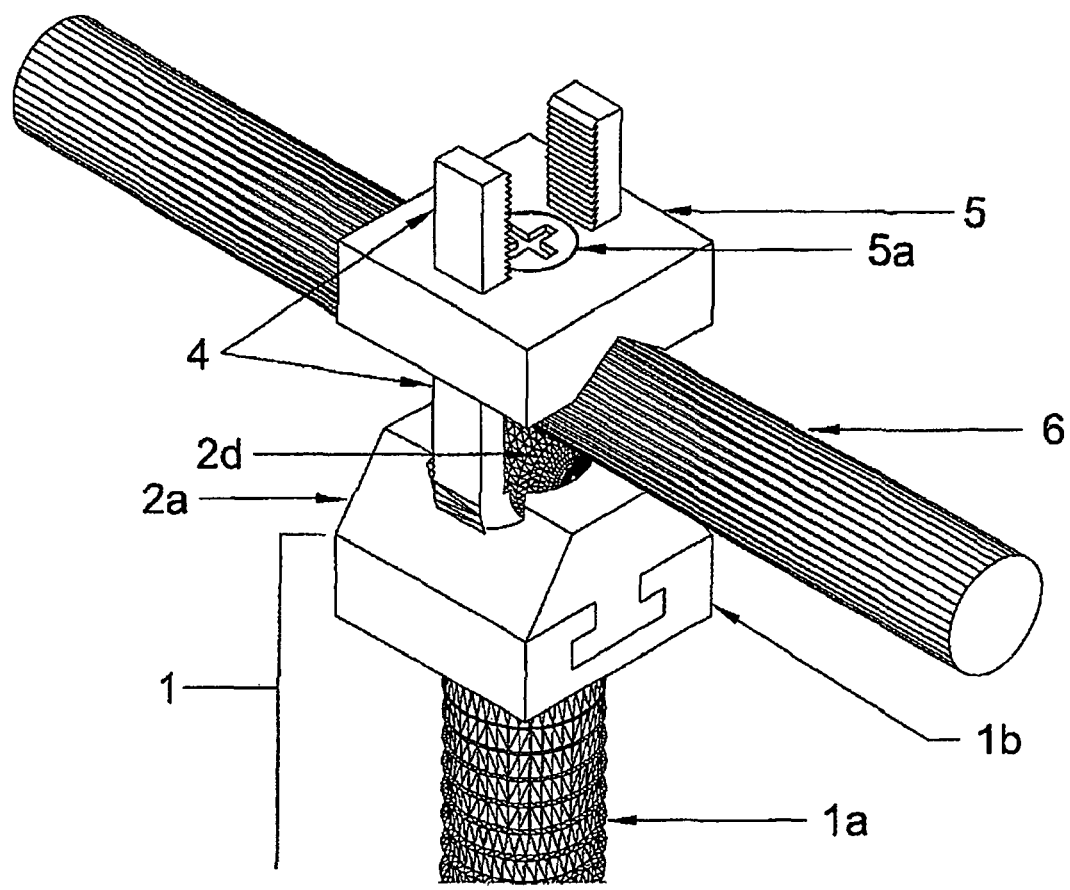
FIG. 1 shows a view of an embodiment of the spinal fixation system, as in place in one of two adjacent vertebra, prior to trimming of the ends of the U-shaped strap. Viewable is an attachment member (1), including an attachment means, represented here as a bone screw (1a) and a docking means (1b), a connector base body (2a), a portion of a ball-shaped member (2d), portions of a U-shaped strap (4), a capture member (5), including a set screw (5a), and a support member, represented here as a rod (6).
Figure 2:
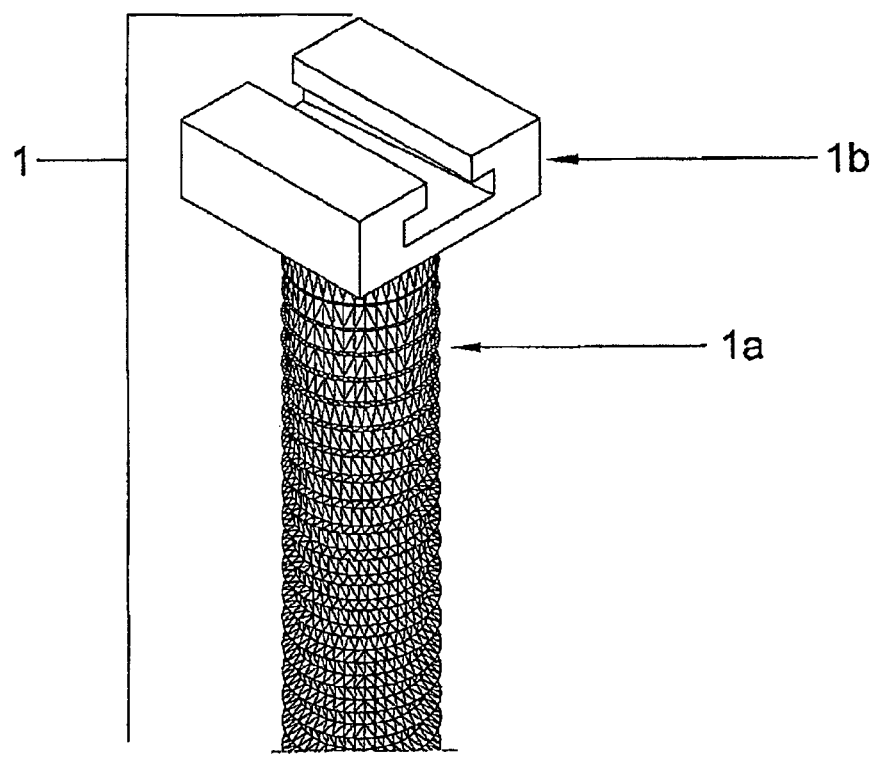
FIG. 2 shows a more detailed view of the attachment member with attachment means (1a) and docking means (1b).
Figure 3A:
FIG. 3a-d shows various views of the attachment member. In the side view, threads are shown for illustrative purpose only. In the top view, note the taper.
Figure 3B:
Figure 3C:
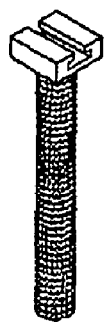
Figure 3D:

The invention provides a new spinal fixation system that overcomes limitations of the currently available systems. The system has a modular construction to allow universal application to varying spine anatomy and load requirements of individual vertebral attachment members, while reducing requirements for large inventories to optimize spinal fixation. Modularity allows the individual attachment members, once attached optimally to bone, to be attached to a variety of interconnecting structural members optimized for load carrying capacity.

The invention provides a spinal fixation system comprising a plurality of fixation members connected to a support member. Each fixation member comprises an attachment member, a connector base attached thereto, a tension strap secured to a body, and a capture member. The support member may comprise rods and/or plates. The attachment member comprises attachment means for fixation to the vertebra and a docking member for attachment to the connector base. The connector base comprises means for attachment to the docking member, a body member that allows for the fixed or mobile attachment of a tension strap used to attach to the support member. The capture member comprises a body having a lower surface and an upper surface, the body having a first set of holes therethrough for receiving the tension strap and a second hole containing a locking member.

In various embodiments, fixation of the attachment member may be any of the well-known means for vertebral attachment, including without limitation a screw, a hook, a wire, or a clip. In various embodiments, the docking member comprises a body having a T-shaped Morse Taper slot, or may alternatively have another shape that allows attachment to the connector base. For example, the docking member may be a tab of any shape that allows insertion within a complementary slot-shaped attachment means on the connector base. The abutting surfaces containing the docking means of the attachment member and the attachment means of the connector base may be of any shape as long as they connect the two components together.

The body of the connector base secures a fixed or mobile tension strap that secures the interconnecting support member. The mobile tension strap embodiment of the connector base system has a "ball-shaped" member, which may, in various embodiments, be spherical in shape, as shown in the drawings, or may be elliptical or cylindrical, any of which may be dimpled to allow for discrete points of fixation to the interconnecting support member, as long as it allows passage of the tension strap around it. In certain preferred embodiments, the "ball-shaped" member may be of a deformable memory shape which allows infinite dimple points of fixation to the rod member. The "ball-shaped" member may be integral with the connector base, i.e. of the same casting, or may be secured to the capture member, e.g. by pins or other attachment means.

In various embodiments, the tension strap has a smooth first portion for passage through the channel between the connector base body and the ball-shaped member. The smooth first portion of the tension strap may be of uniform cross-section, or may employ a varying cross-section (e.g. a bulge or triangular cross-section) to enhance capture of the support member or to satisfy mechanical strength considerations. The upper sections of the tension strap may have latitudinal ridges. The latitudinal ridges on the upper sections of the tension strap may be uniform, or may be upturned or otherwise directional jagged ridges. Alternatively, the upper sections of the U-shaped strap may have latitudinal grooves.

In various embodiments, the first set of holes in the capture member may have grooves on interior sides of the holes that are complementary to the ridges of the upper section of the U-shaped strap. Alternatively, the first set of holes in the capture member may have ridges on interior sides of the holes that are complementary to the grooves of the upper section of the U-shaped strap.

Figure 10:
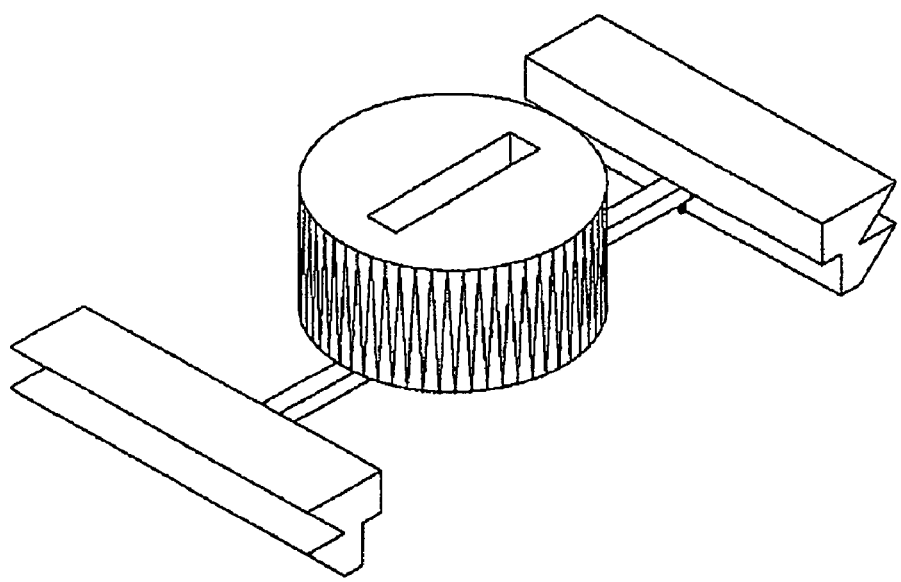
FIG. 10 shows a detailed view of a locking module.

The locking member of the capture member may be a cam locking mechanism. In some embodiments, the cam locking mechanism of the capture member may be a simple threaded member that contacts the interconnecting support member through the second (threaded) hole of the capture member. Alternatively, the cam locking mechanism, when threaded through the second hole, may tighten a deformable memory alloy disc-shaped spring that engages the transverse ridges of the U-shaped strap (see FIG. 9). In yet another embodiment, a two-dimensional wedge of the locking screw may be employed to engage the transverse ridges of the U-shaped strap (see FIG. 10). These latter two embodiments may be combined, i.e. the wedge of the set screw may be of the deformable memory alloy material. In another embodiment, there may exist an elastic member that functions as a spring in a one- or two-dimensional engagement fashion.

Figure 4:
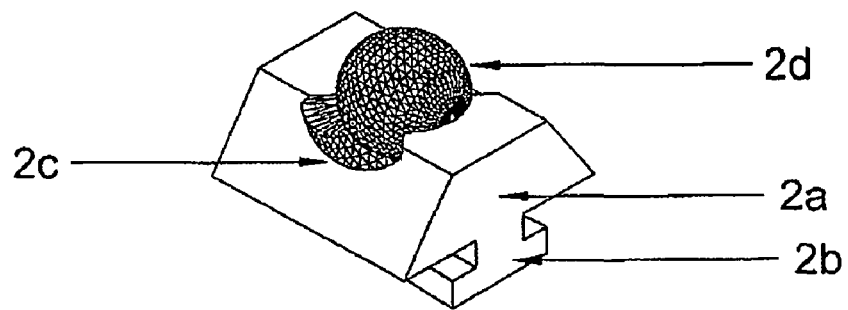
FIG. 4 shows connector base (2) with a body (2a), means for attachment to docking means (2b), with channel (2c) and ball-shaped member (2d).
Figure 5A:
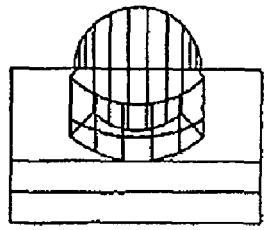
FIGS. 5a-d show various views of the connector base. The side view shows that the spherical shape provides a constant radius between the rod and inside curve of the strap. The top view shows the tapered foot. The front view shows the groove to accept and retain the strap.
Figure 5C:
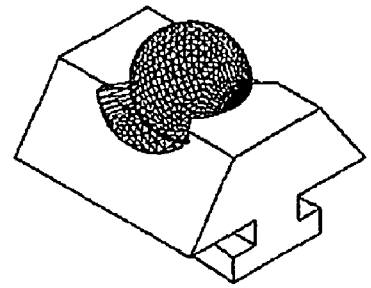
Figure 5B:
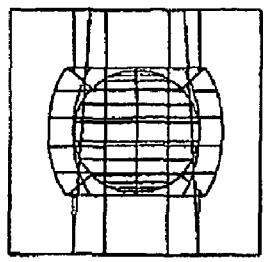
Figure 5D:
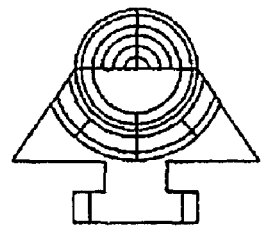
Figure 6:
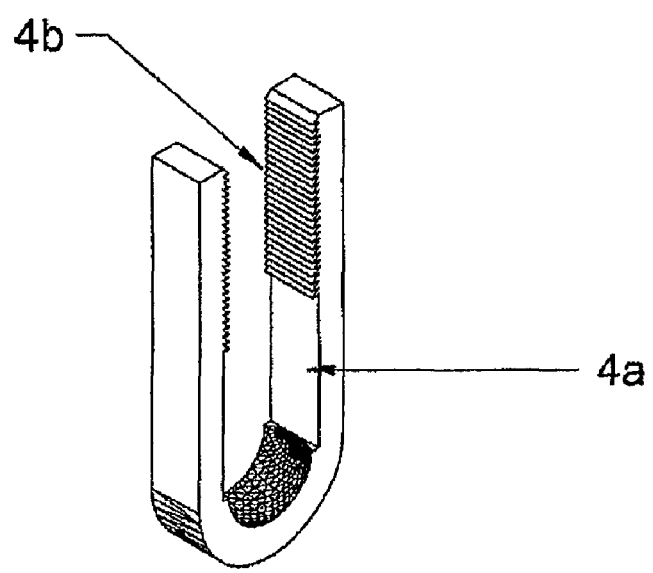
FIG. 6 shows U-shaped strap (4) with a smooth portion (4a) for passage around ball-shaped member and retention of rod and a portion having a plurality of transverse ridges (4b) to engage the capture member (5, FIG. 9).
Figure 7A:
FIGS. 7a-d shows various views of a U-shaped strap, including, in this embodiment, a shaped and textured region for contacting the ball-shaped member (4c).
Figure 7B:
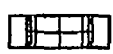
Figure 7C:
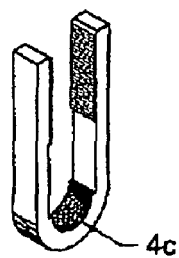
Figure 7D:
Figure 8:
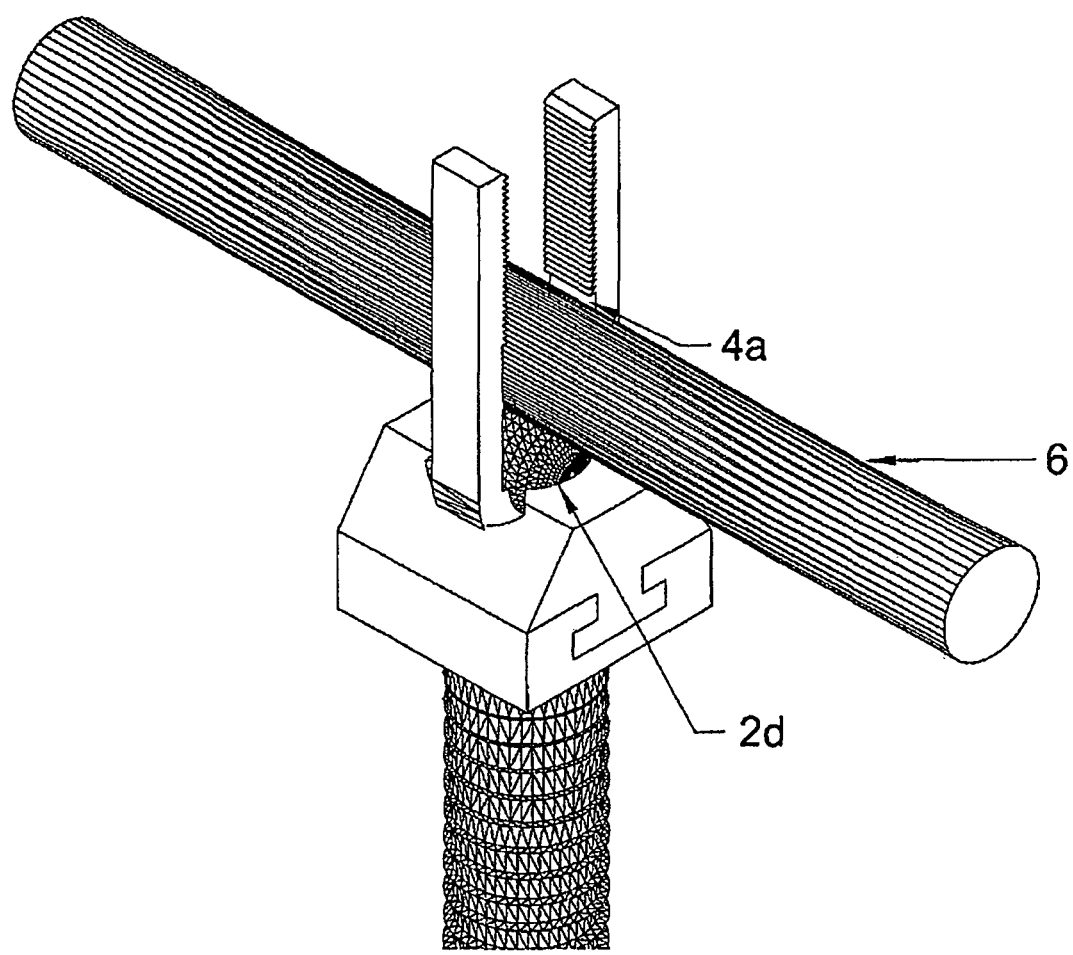
FIG. 8 shows rod (6) in place in part of the smooth portion (4a) of the U-shaped strap and resting on the ball-shaped member (2d) of the connector base.
Figure 9A:
FIGS. 9a-d shows various views of the capture member (5) with a locking mechanism in place (5a) a first V-shaped surface (5b), a second surface (5c) and first holes therethrough (5d) with transverse grooves on an interior side of the holes (5e) and a locking module (5f).
Figure 9B:
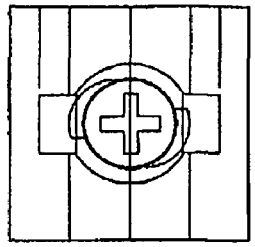
Figure 9C:
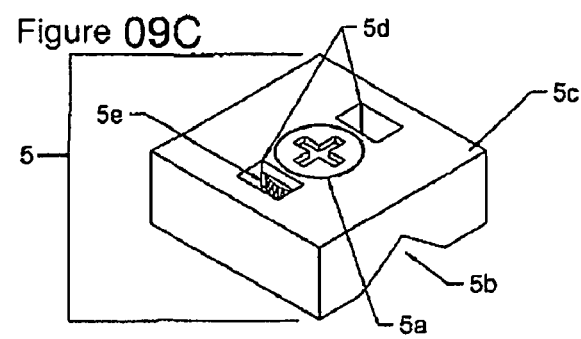
Figure 9D:
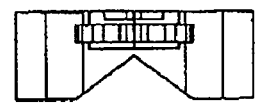

An embodiment of the spinal fixation system shown as in place for one vertebra is shown in FIG. 1. As shown for this embodiment, an attachment member (1) is affixed to the vertebrae, by an attachment means (1a), in this case a screw. A connector base (2) is then slideably inserted into a docking means (1b) of the attachment member by a means for attachment (2b, FIG. 4) on to the connector base. A U-shaped tension strap (4) is attached to the connector base via a ball-shaped member (2d) of the connector base. A rod (6) is then inserted through a smooth portion (4a, FIG. 6) of the U-shaped strap. A capture member (5) is then placed over a portion of the U-shaped strap having a plurality of transverse ridges (4b, FIG. 6) via first holes (5d, FIG. 9) of the capture member (5e, FIG. 9). A V-shaped surface (5b, FIG. 9) of the capture member is snugged down against the rod, and affixed by a cam mechanism (5a, FIG. 9) or spring module (5f, FIG. 9; also FIG. 10) in the capture member. Any portions of the upper portion of the U-shaped tension strap having transverse ridges that extends beyond the second surface (5c, FIG. 9) of the capture member can then be trimmed away.

Materials for the various components of the system may be any of those conventionally used for spinal fixation systems, or any other materials having proper mechanical properties.

What is claimed is:

1. A spinal fixation system comprising a plurality of fixation members connected by a support element, wherein each fixation member comprises an attachment member, a connector base slideably attached thereto, a tension strap and a capture member, wherein the attachment member comprises attachment means for attachment to a vertebra and a docking member for slidable attachment to the connector base; wherein the connector base comprises means for slidable attachment to the docking member, a body, a ball-shaped member, and a channel disposed between the ball-shaped member and the body, wherein the tension strap passes through the channel and around the ball-shaped member and has upper sections that extend beyond the ball-shaped member for attachment to the capture member, wherein the capture member comprises a body having a lower surface and an upper surface, the body having a first set of holes there through for receiving the tension strap and a second hole containing a locking member.

2. The spinal fixation system according to claim 1, wherein the attachment means of the attachment member is selected from a screw, a hook, a wire, or a clip.

3. The spinal fixation system according to claim 1, wherein the docking member comprises a body having a T-shaped Morse Taper slot.

4. The spinal fixation system according to claim 1, wherein the docking member comprises a body having a tab.

5. The spinal fixation system according to claim 1, wherein the ball-shaped member of the connector is of a spherical, elliptical, or cylindrical shape.

6. The spinal fixation system according to claim 1, wherein the ball shaped member is dimpled.

7. The spinal fixation system according to claim 1, wherein the tension strap has a smooth first portion for passage through the channel between the connector base body and the ball-shaped member.

8. The spinal fixation system according to claim 1, wherein the tension strap has upper sections with latitudinal ridges.

9. The spinal fixation according to claim 1, wherein the tension strap has upper sections with latitudinal grooves.

10. The spinal fixation system according to claim 8, wherein the first set of holes in the capture member have grooves on interior sides of the holes that are complementary to the ridges of the upper section of the tension strap.

11. The spinal fixation system according to claim 9, wherein the first set of holes in the capture member have ridges on interior sides of the holes that are complementary to the grooves of the upper section of the tension strap.

12. The spinal fixation system according to claim 1, wherein the locking member of the capture member is a cam locking mechanism.

13. The spinal fixation system according to claim 12, wherein the cam locking mechanism, when threaded through the second hole, tightens a deformable memory alloy disc-shaped spring that engages the latitudinal ridges of the tension strap.

14. The spinal fixation system according to claim 12, wherein the cam locking mechanism has a locking screw with a two-dimensional wedge employed to engage the transverse ridges of the tension strap.

15. The spinal fixation system according to claim 1 or 5, wherein the ball-shaped member of the connector is of a memory deformable shape.

* * * * *